(12) United States Patent
Rolland

(10) Patent No.: US 8,940,131 B2
(45) Date of Patent: Jan. 27, 2015

(54) SCREW COMPRESSION PROCESS FOR THE CONVERSION OF LIGNOCELLULOSIC SUSPENSIONS CONTAINING A HIGH PROPORTION OF DRY MATERIAL

(71) Applicant: IFP Energies Nouvelles, Rueil-Malmaison Cedex (FR)

(72) Inventor: Matthieu Rolland, Vernaison (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 14/067,448

(22) Filed: Oct. 30, 2013

(65) Prior Publication Data
US 2014/0106412 A1    Apr. 17, 2014

Related U.S. Application Data

(62) Division of application No. 12/809,483, filed as application No. PCT/FR2008/001525 on Oct. 29, 2008, now Pat. No. 8,623,175.

(30) Foreign Application Priority Data

Dec. 20, 2007   (FR) ...................... 07 09115

(51) Int. Cl.
| | |
|---|---|
| *D21C 1/00* | (2006.01) |
| *D21C 3/22* | (2006.01) |
| *B30B 9/06* | (2006.01) |
| *C12P 19/02* | (2006.01) |
| *C12P 7/02* | (2006.01) |
| *B30B 9/12* | (2006.01) |
| *D21C 9/18* | (2006.01) |

(52) U.S. Cl.
CPC . *D21C 3/224* (2013.01); *B30B 9/06* (2013.01); *C12P 19/02* (2013.01); *C12P 7/02* (2013.01); *D21C 3/22* (2013.01); *B30B 9/12* (2013.01); *D21C 9/18* (2013.01)
USPC .............................................. 162/42; 162/45

(58) Field of Classification Search
USPC ............................... 162/42, 45; 435/105, 155
See application file for complete search history.

(56) References Cited

U.S. PATENT DOCUMENTS 4,025,356 A * 5/1977 Nyman et al. .................... 127/1
4,451,331 A   5/1984 Raggam et al.
(Continued)

FOREIGN PATENT DOCUMENTS

| EP | 0358837 A1 | 3/1990 |
|---|---|---|
| EP | 0858880 A2 | 8/1998 |

(Continued)

OTHER PUBLICATIONS

Torget at al., Optimization of Reverse-Flow, Two-temperature, Dilute-Acid Pretreatment to Enhance Biomass Conversion to Ethanol, 1996, Applied Biochemistry and Biotechnology, vol. 57/58, p. 85-101.*

(Continued)

*Primary Examiner* — Anthony Calandra
(74) *Attorney, Agent, or Firm* — Millen, White, Zelano & Branigan, P.C.

(57) ABSTRACT

The invention describes a process for the conversion of aqueous suspensions of lignocellulosic solids comprising a solids content of between 1 and 20% of dry material, said process comprising a step a) for compression of said suspension so as to separate the liquid phase present in and between the solids from the compressed solid phase and a step b) for extraction of at least the liquid phase, said liquid phase then being homogenized by heat and/or chemical treatments and reinjected on to the compressed solid phase.

10 Claims, 4 Drawing Sheets

(56) References Cited

U.S. PATENT DOCUMENTS

| | | | |
|---|---|---|---|
| 6,022,419 A * | 2/2000 | Torget et al. | 127/37 |
| 6,145,766 A | 11/2000 | Mraz et al. | |
| 2004/0060673 A1 | 4/2004 | Phillips et al. | |
| 2004/0112554 A1 | 6/2004 | Snekkenes et al. | |
| 2006/0177917 A1 | 8/2006 | Warzywoda et al. | |
| 2008/0121359 A1 | 5/2008 | Holtzapple et al. | |
| 2008/0227161 A1 * | 9/2008 | Levie et al. | 435/95 |

FOREIGN PATENT DOCUMENTS

| | | |
|---|---|---|
| EP | 1690944 A1 | 8/2006 |
| FR | 2347489 A | 11/1977 |
| GB | 1571700 A | 7/1980 |
| WO | 9000213 A1 | 1/1990 |
| WO | 2005025846 A1 | 3/2005 |

OTHER PUBLICATIONS

Kadar et al., Simultaneous saccharification and fermentation (SSF) of industrial wastes for the production of ethanol, 2004, Industrial Crops and Products, p. 103-110.*

World Intellectual Property Office. "International Search Report." PCT/FR2008/001525, Applicant: IFP, Mailed Jun. 18, 2009.

World Intellectual Property Office. "Written Opinion." PCT/FR2008/001525, Applicant: IFP, Mailed Jun. 18, 2009.

* cited by examiner

FIGURE 4
figure 4 a
figure 4b
figure 4c
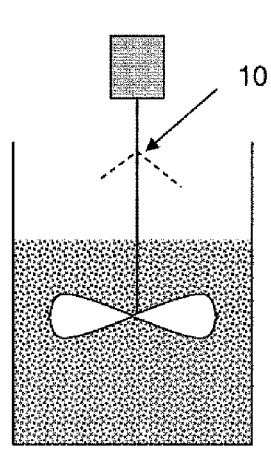
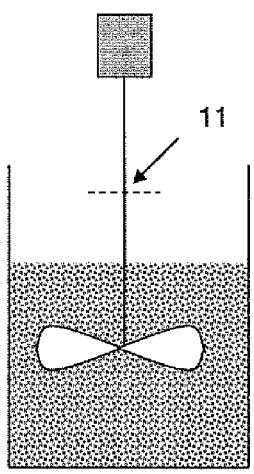
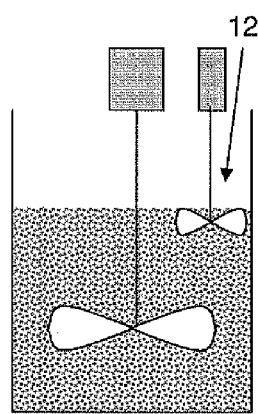

SCREW COMPRESSION PROCESS FOR THE CONVERSION OF LIGNOCELLULOSIC SUSPENSIONS CONTAINING A HIGH PROPORTION OF DRY MATERIAL

TECHNICAL FIELD

The invention concerns a process for the conversion of aqueous suspensions of lignocellulosic solids comprising a solids content of between 1 and 20% of dry material, said process comprising a step a) for compression of said suspension so as to separate the liquid phase present in and between the solids from the compressed solid phase and a step b) for extraction of at least the liquid phase, said liquid phase then being homogenised by heat and/or chemical treatments and reinjected on to the compressed solid phase.

The invention therefore concerns the field of processes for the conversion of a suspension of lignocellulosic solids containing a high proportion of solids, expressed as a percentage of the dry material, said processes being particularly attractive in the case of reactions which are limited by the reactants and/or inhibited by the reaction products.

The expression dry material is used to denote the amount of insoluble material initially added with respect to the total weight of the reaction mixture.

In accordance with the present invention the dry material is constituted by insoluble material and in particular granular solids which in aqueous suspension occur in the form of compressible lumps or flocks. Those granular solids are advantageously formed by:

lignocellulosic biomass before or after pre-treatment and in particular paper pulp, straw and/or cereal bran, sugar cane bagasse, beetroot pulp or wood shavings.

The aqueous suspensions of lignocellulosic materials have a rheology which depends on the solid content and more particularly the amount of cellulose which swells when it is dissolved.

Paper pulp which contains 70% of cellulose is worked in paper pulp factories at levels of concentration in respect of solids of less than 4-5% DM (dry material). At those levels of concentration the suspensions behave like liquids and are used with conventional simple technologies: pumps, pipes, vessel-type reactors and agitators. At higher levels of concentration the water-paper pulp mixtures are composed of lumps of solid soaked with water and in contact with each other and involving little adhesion to each other. The mixture has neither the flow properties of liquids nor those of divided dry solids. In particular agitation is very difficult: either the mixing internals cause the pulp to move in a block type of movement (no agitation) or they shear the pulp into a plurality of blocks. Working with those mixing procedures is a delicate operation: the pumps are replaced for example by endless screws or belts or bucket-type devices. That type of mixing is in fact implemented in a temporary fashion, either in a drying operation and when producing a dry solid (60-90% DM), or when dissolving a dry solid.

The other lignocellulosic biomasses generally contain 30% of cellulose, so that they swell less and can be worked with like liquids up to contents of dry material of about 10%.

The object of the present invention is to provide a process for the conversion of suspensions of lignocellulosic solids comprising a high proportion of solids expressed as a percentage of dry material in such a way as to permit treatments in ranges in which the reactions are usually incomplete, in which the distribution of the reactants and the phenomena involved in inhibition by concentration of the products lead to slower kinetics and/or less attractive reaction yields.

Another object of the invention is to carry out said process for the enzymatic hydrolysis reaction.

Prior Art:

U.S. Pat. No. 7,267,049 B2 describes an apparatus of press type for reducing the amount of water in a pulp by means of a screw system. The liquid phase and the concentrated solid phase are extracted separately.

The present invention utilises that property of screw systems for promoting reactions in a pasty or pulpy medium but it is distinguished in particular in that separation is temporary and the solid is again mixed with the homogenised liquid so as to improve the yield and/or selectivity of the reaction.

U.S. Pat. No. 7,217,340 B2 belongs to a different field from that of the conversion of a suspension of lignocellulosic solids comprising a high proportion of solids and describes a softening composition and its use in the treatment of cellulosic materials containing fibres such as paper, textiles and fabric samples. In particular, in that patent, the proportion of fibre in the paper pulp is increased to 7% of dry material by pressing under vacuum and up to 25% of dry material by being passed into rollers compressing the pulp into a sheet. This therefore involves a final treatment.

Enzymatic hydrolysis is an enzymatic reaction for the conversion of the cellulosic substrate (solid) into cellobiose (intermediate product) and then into glucose (final sugar). The enzymes produce the highest levels of performance in a narrow range of temperature and pH, generally 50-60° C. and pH=4.5-5.5. The reactions are inhibited by the final sugar and very severely inhibited by the cellobiose, the levels of inhibition increasing with the local concentrations.

Concerning enzymatic hydrolysis of lignocellulosic biomass, the maximum proportion of solid expressed as a percentage of dry material which is generally accepted is 2 to 5%. Beyond that the following problems occur:

local increase in the proportions of cellobiose, a reaction intermediate which inhibits the cellulose hydrolysis reactions, local increase in the proportions of glucose, a product of the reaction, which also inhibits the conversion reactions, non-homogeneity of distribution of the enzymes, non-homogeneity of the pH, leading to operations which provide higher or lower levels of performance according to the locations, and non-homogeneity of temperatures.

All those limitations increase with the proportion of dry material. Now, it is of economic interest to be able to work at a higher proportion of initial material (more cellulose) as that leads to higher levels of concentration of sugars and consequently higher levels of concentration of alcohol. That makes it possible to reduce the costs of distillation towards pure alcohol, which are significant in the cost price.

Object and Attraction of the Invention

The present invention concerns a process for the conversion of aqueous suspensions of lignocellulosic solids comprising a solids content of between 1 and 20% of dry material, said process comprising a step a) for compression of said suspension so as to separate the liquid phase present in and between the solids from the compressed solid phase and a step b) for extraction of at least the liquid phase, said liquid phase then being treated/homogenised by heat and/or chemical treatments and reinjected on to the compressed solid phase.

The process according to the invention therefore makes it possible to homogenise the conditions of reactions on pulps formed by compressible lumps by complete renewal of the liquid phase present in the lumps and replacement thereof by a homogenised liquid (levels of concentration, pH, temperature, . . . ).

The lumps are pressed so as to discharge the liquid present in the pores of the lumps. The liquid phase recovered in the pressing operation is then easily mixed with a homogenisation of all the parameters which have an influence on the reaction: levels of concentration, pH, temperature, . . . . The homogenised liquid phase is brought into contact again with the compressed lumps constituting the compressed solid phase, which in a few seconds re-absorb any liquid with which they are brought into contact. All the lumps are then exposed to identical reaction conditions which are more favourable to the reaction than before the process was carried into effect.

The process also makes it possible to obtain identical reaction conditions irrespective of the size of the lumps.

DESCRIPTION OF THE FIGURES

FIG. 4 shows the different modes of reinjection and dispersion of the solid phase resulting from extraction step b) at the head of the screw-type reactor, the screw at the vessel bottom not being shown in the Figure.

DETAILED DESCRIPTION OF THE INVENTION

The invention describes a process for the conversion of an aqueous suspension of lignocellulosic solids comprising a solids content of between 1 and 20%, preferably between 1 and 15% and very preferably greater than 8% and still more preferably between 8 and 15% of dry material, the process comprising a step a) for compression of the suspension so as to separate the liquid phase present in and between the solids from the compressed solid phase and a step b) for extraction of at least the liquid phase, the liquid phase then being homogenised by heat and/or chemical treatments and re-mixed with the solid phase.

The compression step a) is advantageously carried out in accordance with a vertical compression axis or in a screw.

The step a) is also advantageously performed with agitation to improve homogenisation.

The liquid phase collected is advantageously injected in dispersed manner so as to uniformly sprinkle the upper surface of the solid phase. Dispersion is advantageously implemented by a system of feed nozzles which generate uniformly distributed drops.

The description of the invention is set forth with reference to FIGS. 1 to 4.

Figure 1:
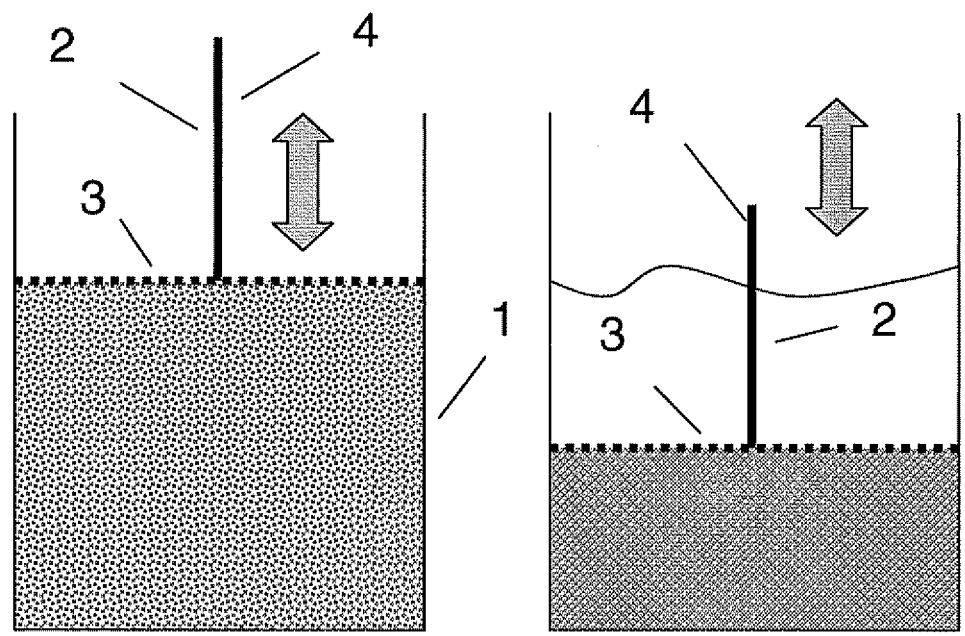
FIG. 1 shows an embodiment of the piston-type reactor in which the reaction for the conversion of aqueous lignocellulosic suspension and compression step a) of the process according to the invention take place.
Figure 2:
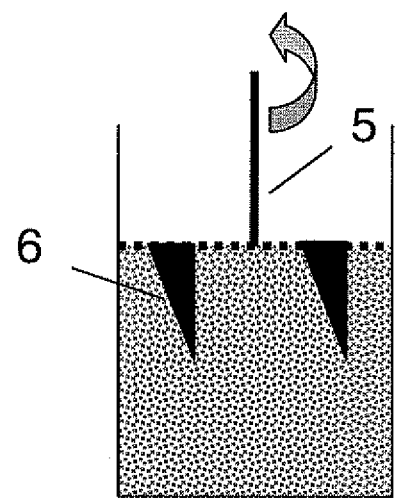
FIG. 2 shows the embodiment of the piston-type reactor in which the piston is a rotary piston and also illustrates the mixing means consisting of protuberances projecting on a part at least of the height of the compressed solid phase.

In accordance with a first embodiment shown in FIG. 1 compression step a) of the process according to the invention is advantageously performed in a reactor 1 comprising a perforated compression piston 2, the compression piston comprising 3 distinct components:

a perforated grill (3) which allows the liquid to pass and which blocks the lumps, the mean size of the perforations advantageously being between 1 and 3 times the size of the lumps, a grill support, and a compression shaft (4) which is perpendicular to the grill.

Preferably it is not necessary for the grill 3 to arrest all of the lumps. The finest pitch of the grill is 500 p.m. For a smaller grill pitch the liquid flow will be low and the downward movement of the piston excessively slow. The grill 3 is advantageously produced with a perforated plate or with a woven metal meshwork or with a porous material (ceramic, metal sintered) or a polymer diaphragm (hydrophilic or hydrophobic).

The function of the grill support is to transmit the mechanical forces between the grill and the compression shaft which is perpendicular to the grill so as to keep the grill horizontal, to ensure sealing integrity between the walls and the piston, and to allow the liquid to pass.

In this first embodiment the piston 2 is regularly moved downwardly and raised again in the direction of the arrow indicated in FIG. 1. After the downward movement of the piston the liquid phase is above the piston, with the compressed solid phase below it.

The aqueous suspension of lignocellulosic solids may advantageously be agitated: agitation may be implemented in two different ways: either the compression piston 2 may comprise an agitator (not shown in FIG. 1), the drive shaft of which is internal and coaxial with the compression shaft of the piston 2, or the compression piston is a rotary compression piston 5 provided with protuberances 6 projecting over a part at least of the height of the aqueous suspension of lignocellulosic solids.

The liquid phase is naturally at least partially homogenised in the compression step a) by virtue of its passing through the lumps of lignocellulosic solids and through the grill 3.

Advantageously step b) for extraction of the liquid phase is effected by taking off the liquid phase on the outside of the reactor (2), followed by reinjection by means of a pump and an injector. The taking-off and injection flow rate is adjusted so that the volume of the reactor is pumped at least 3 times and preferably 10 times before the piston is raised again.

So as to improve the homogeneity of the liquid phase the compression shaft 4 of the rotary compression piston may advantageously be provided with blades above the grill.

Indeed the pumping effect is at a maximum at the beginning, in the first hour. Then, as the reaction progresses, the solid content decreases greatly and the pumping effect is of lesser interest. It may therefore be advantageous to totally raise the piston and operate in the usual manner, namely using solely a conventional agitator.

In the case where the process according to the invention is performed in a piston-type reactor described hereinbefore, the period of time between the pumping operations is advantageously, for the first hour, between 1 and 10 minutes and preferably between 2 and 7 minutes and then between 5 and 120 minutes, and preferably between 10 and 60 minutes.

Figure 3:
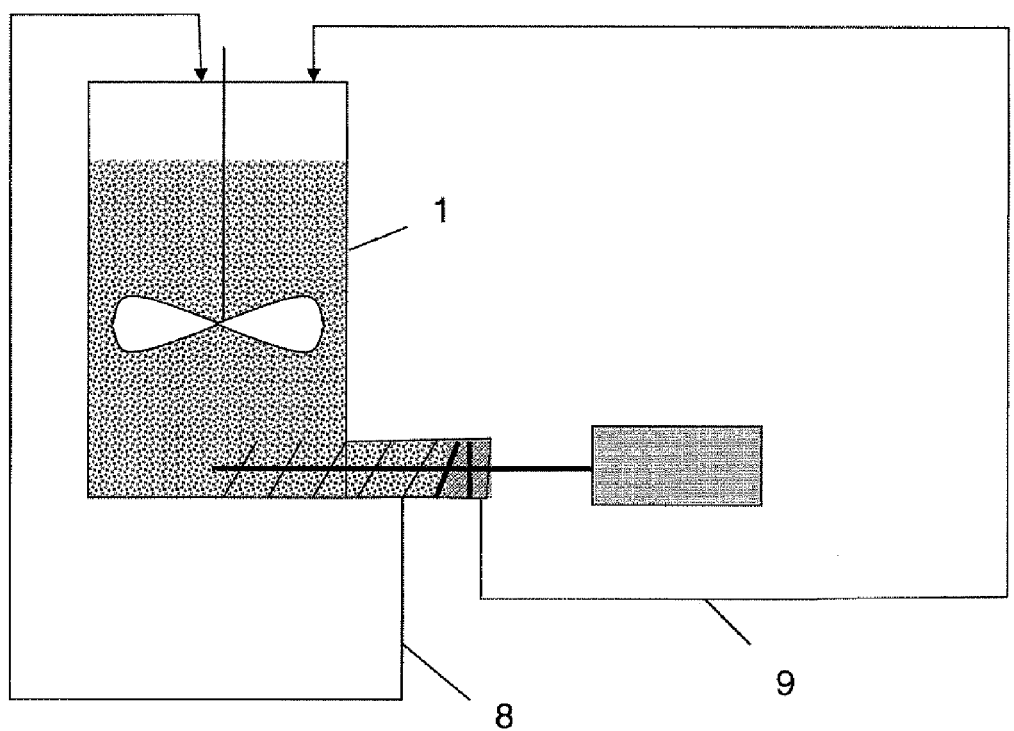
FIG. 3 shows the embodiment of the screw-type reactor in which the reaction for conversion of the aqueous lignocellulosic suspension and compression step a) of the process according to the invention take place.
Figure 5:
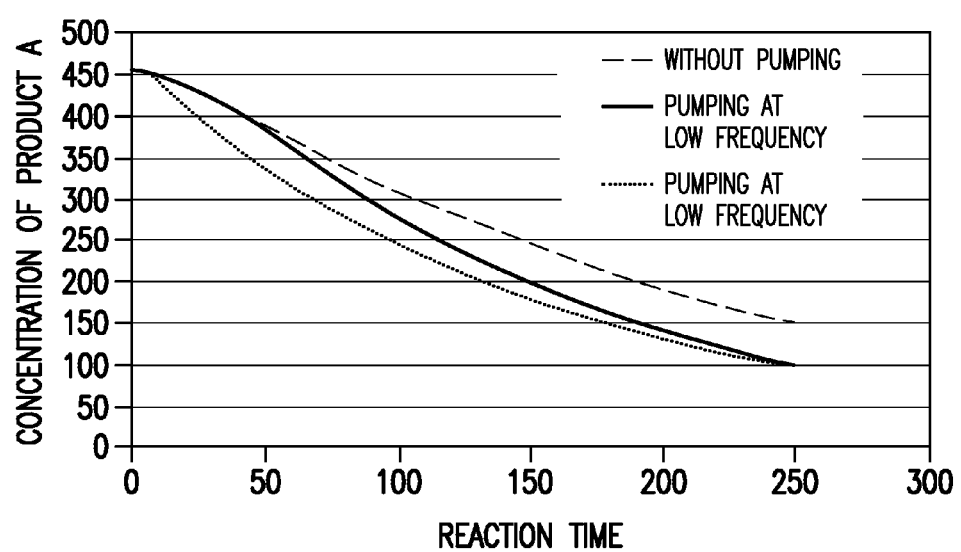
FIG. 5 shows the concentration of product A in dependence on the reaction time in accordance with Example 3.

In a second embodiment illustrated in FIG. 3 the compression step a) is performed in a reactor 1 comprising a screw 7 at the bottom of the vessel in which the compression step a) takes place. In that case separate collection of the liquid phase (conduit 8) and the compressed solid phase (conduit 9) is advantageously effected at the discharge from compression step a). In fact the compressed solid phase is also advantageously extracted, preferably continuously, in the extraction step b), and reinjected at the head of the reactor by way of the conduit 9.

In a first preferred embodiment of this second configuration shown in FIG. 4a the compressed solid phase is advantageously reinjected and dispersed at the head of the reactor, preferably by means of a static or rotary dispersion cone 10, with a half-angle at the top of between 30 and 60° and of a diameter of between ⅓ and ¼ of the diameter of the reactor or preferably by means of a rotary dispersion plate 11 of a diameter of between ⅓ and ¼ of the diameter of the reactor, the plate being driven by the drive shaft of the agitator as shown in FIG. 4b.

In accordance with another preferred configuration of the second embodiment as shown in FIG. 4c the compressed solid phase is advantageously reinjected and dispersed at the head of the reactor by means of a secondary mixer 12 dedicated to bringing the solid phase into intimate contact with the liquid phase.

The collected liquid phase is advantageously injected in dispersed fashion so as to uniformly sprinkle the upper surface of the solid phase. Dispersion is advantageously effected by a system of feed nozzles which generate uniformly distributed drops.

In the case where the process according to the invention is performed in a screw-type reactor as described hereinbefore the rate of renewal by the screw, during the first two hours, is between one reactor volume every minute and one reactor volume every 30 minutes and preferably between one reactor volume every 5 minutes and one reactor volume every 20 minutes and then between one reactor volume every 20 minutes and one reactor volume every 60 minutes and preferably between one reactor volume every 30 minutes and one reactor volume every 50 minutes.

Irrespective of the mode of implementation of the compression step and in accordance with the invention the liquid phase is homogenised by heat and/or chemical treatments before being re-mixed with the solid phase.

The heat and/or chemical treatments which are advantageously carried out on the extracted liquid phase are as follows:
- temperature regulation by means known to the man skilled in the art,
- regulation of the pH by means known to the man skilled in the art, and
- addition of reactants such as for example antibiotics.

Another object of the invention is to carry out that process for the enzymatic hydrolysis reaction. In that case the enzymatic hydrolysis reaction described hereinbefore takes place in the piston-type or screw-type reactor described hereinbefore.

Advantageously an alcoholic fermentation reaction also takes place in that piston-type or screw-type reactor at the same time as the enzymatic hydrolysis reaction.

The lignocellulosic biomass may advantageously be subjected to a pre-treatment step such as for example chemical, thermal and mechanical operations intended to enhance the yields of the enzymatic hydrolysis reaction. Those pre-treatments necessitate handling pulps and pastes which are more or less dry according to the circumstances involved. Such pre-treatments may be for example baking operations in an acid or basic phase, compression-expansion operations (vapour explosion, AFEX process), . . . . Generally the products resulting from the pre-treatment steps are solids of grain or lump type or pulps with a high water content. The invention thus opens up potentialities in regard to intermediate treatments with the production or implementation of pulp and paste with a high proportion of dry matter.

Advantageously the heat and/or chemical treatments performed on the liquid phase extracted at the end of the enzymatic hydrolysis reaction are as follows:
- the liquid phase can advantageously pass into a process for conversion of the cellobiose into glucose so as to effect additional enzymatic hydrolysis on the outside of the reactor; and
- after a change in the operating conditions, in accordance with procedures known to the man skilled in the art, the liquid phase may pass into a separate fermentation process, the effluent from the fermentation step then being reinjected at the reactor head after re-adjustments of the operating conditions (pH, temperatures . . . ), to the operating conditions of enzymatic hydrolysis in accordance with procedures known to the man skilled in the art.

EXAMPLES

Example 1

Enzymatic Hydrolysis

The enzymatic hydrolysis reaction is performed in the reactor with an extraction screw at the bottom of the vessel in accordance with the process of the invention, the suspension of lignocellulosic solids being formed by a suspension of paper pulp containing 15% of insoluble material, with addition of the raw material progressively.

The operating conditions in the screw-type reactor are as follows:
temperature of the reactor 55° C.,
pH=4.8.
Rate of renewal by the screw is:
during the first two: 1 volume of reactor in 20 minutes,
and then: 1 volume of reactor in 50 minutes.

The extracted liquid phase is subjected to a treatment for adjustment of the pH in accordance with a procedure known to the man skilled in the art.

Example 2

Enzymatic Hydrolysis

The enzymatic hydrolysis reaction is performed in the piston-type reactor according to the process of the invention, the suspension of lignocellulosic solids being formed by a suspension of wood shavings containing 13% of insoluble material, addition of the raw material being progressive.

The operating conditions in the screw-type reactor are as follows:
temperature of the reactor 55° C.,
pH=4.8.
The period of time between the pumping operations is as follows:
the first hour: 1 pumping operation every 5 minutes, and
then: 1 pumping operation every 30 minutes.

Example 3

Model with Diffusional Limitation in Respect of Reactant

This simulation demonstrates the effectiveness of the process according to the invention which makes it possible to render uniform the concentration of reactant A when the conversion process is performed in a piston-type reactor in relation to a process which does not include step b) for extraction of the liquid phase, nor homogenised by heat and/or chemical treatments and re-injection thereof on to the solid phase.

The chemical reaction carried out in the piston-type reactor described hereinbefore is a chemical reaction, the kinetics of which are of first order. The concentration of a reactant A in suspension in the liquid phase is measured. Diffusion of the reactant A into the lump is slow and limits the rate at which the reactant A disappears: the core of the lump does not involve optimum working.

The modelling shows that regular pumping makes it possible to improve the levels of yield (that is to say a larger amount of A is consumed in the same time or as much A is consumed in a shorter time), that being the case so much more in proportion to the pumping frequency being increased.

Compressing of the lumps in accordance with the process of the invention therefore makes it possible to render uniform the concentration of A in the lump and on the outside of the lump so that the diffusional limitations which limit the reaction are minimised.

The invention claimed is:

1. A process for the conversion of aqueous suspensions of lignocellulosic solids comprising a solids content of between 1 and 20% of dry material, said process comprising a step a) for compression of said suspensions so as to separate liquid phase present in and between the solids from the compressed solid phase and a step b) for extraction of at least the liquid phase, said liquid phase then being homogenised by heat and/or chemical treatments and re-mixed with the solid phase, said compression a comprising being conducted by a screw compression in a reactor comprising a screw, and wherein the compressed solid phase is also extracted in the extraction step b) and reinjected at the head of the reactor.

2. A process according to claim 1 wherein the compression step a) is carried out in accordance with a vertical compression axis.

3. A process according to claim 1 wherein the compressed solid phase is reinjected and dispersed at the head of the reactor.

4. A process according to claim 3 wherein the compressed solid phase is reinjected by means of a static or rotary dispersion cone, with a half-angle at the top of between 30 and 60° and of a diameter between ⅓ and ¼ of the diameter of the reactor.

5. A process according to claim 3 wherein the compressed solid phase is reinjected by means of a rotary dispersion plate of a diameter of between ⅓ and ¼ of the diameter of the reactor, said plate being driven by the drive shaft of the agitator.

6. A process according to claim 1, said compression comprising carrying out an enzymatic hydrolysis reaction.

7. A process according to claim 6 wherein an alcoholic fermentation reaction also takes place simultaneously with the enzymatic hydrolysis reaction.

8. A process according to claim 7 wherein the liquid phase passes into a process for conversion of the cellobiose into glucose so as to effect additional enzymatic hydrolysis at the outside of said reactor.

9. A process according to claim 6 in which the liquid phase passes into a separate fermentation process, and effluent from the fermentation process then being reinjected at the head of the reactor.

10. A process according to claim 7 in which the liquid phase passes into a separate fermentation process, and effluent from the fermentation process then being reinjected at the head of the reactor.

* * * * *

UNITED STATES PATENT AND TRADEMARK OFFICE
CERTIFICATE OF CORRECTION

PATENT NO.           : 8,940,131 B2
APPLICATION NO.      : 14/067448
DATED                : January 27, 2015
INVENTOR(S)          : Matthieu Rolland It is certified that error appears in the above-identified patent and that said Letters Patent is hereby corrected as shown below:

In the Claims

Column 7, Line 31 reads: "phase, said compression a comprising being conducted by a" should read -- phase, said compression comprising being conducted by a --.

Signed and Sealed this
Twenty-sixth Day of May, 2015

Michelle K. Lee
*Director of the United States Patent and Trademark Office*